(12) United States Patent
Schoon et al.

(10) Patent No.: US 8,124,058 B2
(45) Date of Patent: Feb. 28, 2012

(54) ARTIFICIAL NAIL COMPOSITIONS AND RELATED METHODS

(75) Inventors: Douglas Dean Schoon, Laguna Miguel, CA (US); George Frederick Cowperthwaite, East Fallowfield, PA (US); Allen David Johnston, Westchester, PA (US); Susan C. Sheariss, Swedesboro, NJ (US); Jennifer Ellen Moore, La Jolla, CA (US)

(73) Assignee: Creative Nail Design, Inc., Vista, CA (US)

( * ) Notice: Subject to any disclaimer, the term of this patent is extended or adjusted under 35 U.S.C. 154(b) by 2026 days.

(21) Appl. No.: 10/988,990

(22) Filed: Nov. 15, 2004

(65) Prior Publication Data

US 2008/0241083 A1    Oct. 2, 2008

Related U.S. Application Data

(63) Continuation of application No. 09/037,128, filed on Mar. 9, 1998, now Pat. No. 6,818,207.

(51) Int. Cl.
*A61K 8/00* (2006.01)
*A61Q 3/00* (2006.01)
(52) U.S. Cl. ......................................................... 424/61
(58) Field of Classification Search .................. None
See application file for complete search history.

(56) References Cited

U.S. PATENT DOCUMENTS 4,229,431 A    10/1980    Lee, Jr.
(Continued)

FOREIGN PATENT DOCUMENTS

EP    0085370    8/1983
(Continued)

OTHER PUBLICATIONS

Research Disclosure 35143, "Stable Emulsion Polymers", Jul. 1993.

*Primary Examiner* — Anand Desai
*Assistant Examiner* — Melissa S Mercier
(74) *Attorney, Agent, or Firm* — Pillsbury Winthrop Shaw Pittman LLP

(57) ABSTRACT

The invention comprises a polymerizable monomer composition for application to the nail surface and polymerization thereon to yield an artificial nail structure, comprising at least one multicarbonyl-vinyl containing monomer; a polymerized artificial nail structure having a thickness of about 10-60 mils, and a modulus of elasticity of about 550-800 $N/m^2$, comprising a copolymer of at least one ethylenically unsaturated monomer and a multicarbonyl vinyl-containing monomer; a method for reducing, ameliorating, or eliminating delamination of an artificial nail structure from the natural nail surface; a method for improving adhesion of an artificial nail structure to the nail surface; and a method for reducing premature gelation of a liquid monomer composition.

3 Claims, No Drawings

U.S. PATENT DOCUMENTS

| | | | |
|---|---|---|---|
| 4,260,701 A | | 4/1981 | Lee, Jr. |
| 4,669,491 A | | 6/1987 | Weisberg |
| 5,098,696 A | | 3/1992 | Montgomery |
| 5,185,212 A | | 2/1993 | Spada |
| 5,266,322 A | * | 11/1993 | Myers et al. ............... 424/401 |
| 5,380,520 A | | 1/1995 | Dobbs |
| 5,407,666 A | | 4/1995 | Patel |
| 5,523,076 A | | 6/1996 | Schoon |
| 5,663,266 A | | 9/1997 | Taylor |
| 5,738,843 A | | 4/1998 | Montgomery |
| 5,772,988 A | * | 6/1998 | Pagano et al. ............... 424/61 |
| 5,830,442 A | | 11/1998 | Beaver |

FOREIGN PATENT DOCUMENTS

WO 9742930 5/1997

* cited by examiner

ARTIFICIAL NAIL COMPOSITIONS AND RELATED METHODS

CROSS-REFERENCE TO RELATED APPLICATIONS

This application is a continuation of application Ser. No. 09/037,128, filed on Mar. 9, 1998, now U.S. Pat. No. 6,818,207.

TECHNICAL FIELD

The invention is in the field of compositions for application to nails which polymerize on the nail surface to yield an artificial nail structure and the resulting polymerized artificial nail structure, as well as a method for improving adhesion of the artificial nail to the nail surface, and a method for reducing delamination of the laminate formed when the artificial nail is adhered to the nail surface, and a method for reducing premature gelation of monomer compositions used to make artificial nails.

BACKGROUND OF THE INVENTION

Artificial nails are widely used by women who desire to have long, attractive fingernails which do not break or chip as readily as natural nails. Artificial nails are generally formed directly on the natural nail surface by coating on the nail a layer of a viscous liquid monomer composition comprised of one or more addition polymerizable, ethylenically unsaturated monomers, shaping the material to the desired configuration, then allowing the material to polymerize on the nail surface to yield a hard coating. The resulting artificial nail is then shaped and polished to look like a natural nail. Often the monomer composition comprises one or more esters of acrylic or methacrylic acid and an aliphatic alcohol or ether alcohol, e.g. ethyl acrylate or tetraethylene glycol di-methacrylate.

The preparation and application of artificial nails requires a certain level of skill. In addition, the monomer composition must exhibit certain properties which enable easy application and polymerization of the composition on the nails, while at the same time providing a polymerized nail structure which is strong, yet flexible. Important properties of the monomer composition are gel time, set time, and flexibility. In other words, the monomer composition must reach a certain viscosity in a certain period of time after polymerization is initiated. Otherwise precious minutes are wasted waiting for polymerization to occur, or if the applied monomer composition is not viscous enough when applied to the nail, it will drip off the nail surface and will be difficult to shape. Once the monomer composition is applied to the nails it must set, or polymerize, in a period of time which is adequate to permit a skilled nail technician to apply and shape the composition, but not so long as to have the client waiting for excess periods of time. The monomer composition must be flexible enough so that the nail technician can shape it into the desired configuration prior to setting. The hardened nail structure must be flexible and strong. Flexibility means that the nail can withstand certain amounts of stress without breaking. Too little flexibility causes brittleness and easy breakage. On the other hand, too much flexibility causes reduced strength. Thus, it is important to have a balance between flexibility and strength.

Further, the polymerized artificial nail structure must exhibit adequate adhesion to the nail surface, otherwise it will become dislodged too easily. Generally, artificial nails do not adhere well to nail surfaces. Thus, it is necessary to first coat the nail surface with a primer composition, which is most often acrylic or methacrylic acid alone or in a solvent composition. The primer promotes adhesion of the subsequently applied artificial nail to the nail surface. Obviously, it would be desirable to eliminate use of the primer composition, without lowering adhesion of the artificial nail structure to the nail surface.

Another consistent problem with artificial nails is known as "curling", or more technically described as "delamination". This results when the natural nail surface curves away from the artificial nail as the natural nail grows. This delamination provides crevices between the two surfaces, which tend to collect dirt and bacteria. Delamination is a major cause of infection for those who wear artificial nails. Also, delamination causes discomfort and poor hygiene.

In addition, another problem for manufacturers of artificial nail compositions is polymerization of the monomer composition in the container in which it is sold. This is referred to as "premature gelation" or "premature polymerization". Obviously, product which is polymerized at the time it is received by the nail salon is not suitable for use and is returned to the manufacturer. In some cases, product may be received in the salon which is close to premature polymerization. The salon owner, not realizing this, uses the product to prepare artificial nails. The resulting artificial nails are often deficient in adhesion and strength.

There is a need to improve the gel time, set time, flexibility, strength, adhesion, and other characteristics of artificial nails, as well as to reduce premature gelation and delamination or curling.

It is an object of the invention to provide an artificial nail monomer composition which exhibits improved gel time, set time, and flexibility.

It is an object of the invention to provide a polymerized artificial nail structure which exhibits improved strength, flexibility, and adhesion to the nail.

It is an object of the invention to provide a method for improving adhesion of an artificial nail structure to the nail surface, without the necessity of treating the nail surface with a primer composition.

It is an object of the invention to provide an artificial nail composition which exhibits a reduced tendency toward premature gelation.

It is an object of the invention to provide a method for reducing delamination of the artificial and natural nail surface, or the curling of the natural nail away from the artificial nail structure.

SUMMARY OF THE INVENTION

It has been found that the above stated objectives can be realized in a liquid, artificial nail composition comprised of one or more other addition-polymerizable, ethylenically unsaturated monomers, by also including in the composition a monoethylenically unsaturated vinyl monomer that contains two or more carbonyl groups (hereinafter referred to as a "multicarbonyl vinyl-containing monomer").

The invention also comprises a polymerized artificial nail structure having a thickness of about 10-60 mils, and a modulus of elasticity of about 550-800 N/m$^2$, comprising a copolymer of at least one ethylenically unsaturated monomer and a multicarbonyl vinyl-containing monomer.

The invention comprises a method for reducing, ameliorating, or eliminating delamination of an artificial nail structure from the natural nail surface, wherein said artificial nail structure is obtained by polymerizing on the natural nail surface a polymerizable monomer composition, comprising adding to said polymerizable monomer composition an effective amount of at least one multicarbonyl-vinyl containing monomer.

The invention comprises a method for improving adhesion of an artificial nail structure to the nail surface, wherein the artificial nail structure has been applied by polymerizing on the nail surface a polymerizable monomer composition, comprising adding to said polymerizable monomer composition an effective amount of at least one multicarbonyl-vinyl containing monomer.

The invention comprises a method for reducing premature gelation of a liquid monomer composition containing at least one other ethylenically unsaturated monomer, comprising adding to said composition an effective amount of at least one multicarbonyl-vinyl containing monomer.

DETAILED DESCRIPTION

All parts and percentages mentioned herein are parts and percentages by weight unless otherwise indicated.

The term "nail surface" means the natural nail surface, or a natural nail to which a pre-formed artificial nail or nail tip is adhered. In other words, the polymerizable compositions of the invention may be applied directly to the keratinous surface of the natural nail, or to a nail surface having affixed thereto a pre-formed artificial nail or nail tip enhancement.

The term "mil" means thousandths of an inch.

The term "polymerizable" means that the composition polymerizes on the nail surface upon exposure to appropriate chemicals, heat, light (such as visible or ultraviolet light), or other types of stimuli. The polymerization may occur by free radical or cationic mechanisms.

"Tangent modulus of elasticity", or "modulus of elasticity" means the ratio, within the elastic limit of stress to corresponding strain. The modulus of elasticity is determined using ASTM test method D 790-86, which is entitled "Standard Test Method For Flexural Properties of Unreinforced and Reinforced Plastics and Electrical Insulating Materials", and then calculated by drawing a tangent to the steepest initial straight line portion of the load deflection curve and using the following formula to calculate the value in Newtons per square meter ($N/m^2$) (or pounds per square inch):

$$E_B = L^3 m / 4bd^3$$

where:
$E_B$=modulus of elasticity in bending, $N/m^2$ (or psi)
L=support span, in meters (inches)
b=width of beam tested, in meters (inches)
d=depth of beam tested, in meters (inches)
m=slope of the tangent to the initial straight-line portion of the load deflection curve, N/m (lbf/in) of deflection.

The Polymerizable Composition

The invention comprises a polymerizable monomer composition for application to the nails and polymerization thereon to yield an artificial nail structure. The polymerizable composition is preferably an anhydrous liquid, having the consistency of a semi-mobile gel to freely mobile liquid at room temperature. Immediately prior to use, the polymerizable composition is applied to the nail surface and shaped by the nail technician. After polymerization an artificial nail structure is obtained, which is then shaped and polished. The polymerizable composition of the invention contains at least one multicarbonyl-vinyl containing monomer.

The Multicarbonyl-Vinyl Containing Monomer

The composition contains at least one multicarbonyl-vinyl containing monomer, preferably in the range of about 0.1-98.5%, more preferably 0.5-95%, most preferably 1-15%. The multicarbonyl-vinyl containing monomer includes those having the following general formula:

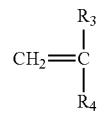

wherein $R_3$ is H, a $C_{1-30}$ straight or branched chain alkyl, aryl, aralkyl; and

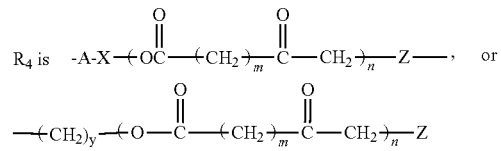

wherein

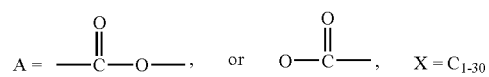

straight or branched chain alkyl, m is 1 to 5, n is 1 to 30, y is 0 to 50; and Z=H or a $C_{1-30}$ straight or branched chain alkyl.

Preferably $R_3$ is hydrogen or a $C_{1-8}$ alkyl, preferably methyl, and $R_4$ is

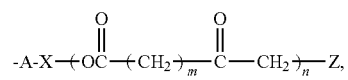

wherein

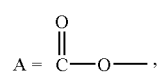

X=$C_{1-5}$ alkylene
m=1-5,
n=1-5, and
Z=$C_{1-10}$ straight chain alkyl.

Most preferably $R_3$ is hydrogen or methyl, and $R_4$ is as defined above wherein:
X=$CH_2CH_2$
m=1
n=1
Z=$CH_3$ In the preferred embodiment of the invention the multicarbonyl-vinyl containing monomer is acetoacetoxyethyl methacrylate, which has the formula:

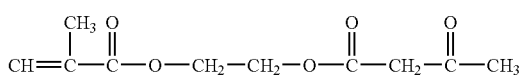

Other Ingredients

The polymerizable compositions may additionally contain a variety of other ingredients, as set forth below:

Another Ethylenically Unsaturated Monomer

The polymerizable composition preferably contains 5-98%, preferably 10-96%, more preferably 25-95% by weight of the total composition of at least one other ethylenically unsaturated monomer. The ethylenically unsaturated monomer may be mono-, di-, tri-, or polyfunctional as regards the addition-polymerizable ethylenic bonds. A variety of ethylenically unsaturated monomers are suitable, so long as the monomers selected are capable of polymerization directly on the nail surface to yield a polymerized artificial nail structure upon exposure to the appropriate stimuli.

Examples of suitable monofunctional ethylenically unsaturated monomers include those of the formula:

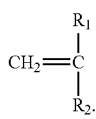

I wherein $R_1$ is H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is H, a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl which may be substituted with one or more hydroxyl groups, or $[(CH_2)_mO]_nH$ wherein m is 1-20, and n is 1-200.

Preferably, the monofunctional ethylenically unsaturated monomer is of Formula I, above, wherein $R_1$ is H or a $C_{1-30}$ alkyl, and $R_2$ is COOM wherein M is a $C_{1-30}$ straight or branched chain alkyl which may be substituted with one or more hydroxy groups.

More preferably, $R_1$ is H or $CH_3$, and $R_2$ is COOM wherein M is a $C_{1-10}$ straight or branched chain alkyl which may be substituted with one or more hydroxy groups. In the preferred embodiment of the invention, the monofunctional ethylenically unsaturated monomer is a mixture of monomers of Formula I where in one monomer $R_1$ is H or $CH_3$ and $R_2$ is COOM where M is a $C_{1-10}$ alkyl, and where in the second monomer $R_1$ is H or $CH_3$, and $R_2$ is COOM where M is a $C_{1-10}$ alkyl substituted with one or more hydroxy groups.

In the preferred embodiment of the invention, the monofunctional ethylenically unsaturated monomer comprises a mixture of one or more methacrylate monomers and one or more hydroxyalkyl methacrylate monomers, preferably about 50-98.5% of a methacrylate monomer, and 5-20% of a hydroxyalkyl methacrylate monomer. Most preferred is a composition containing 60-98.5% ethyl methacrylate and 7-15% hydroxypropylmethacrylate.

Di-, tri- and polyfunctional monomers, as well as oligomers, of the above monofunctional monomers may also be used in the composition. Such di-, tri-, and polyfunctional monomers are generally known as cross-linking monomers because they aid in cross-linking of the monomer composition during and after polymerization. Preferred difunctional monomers include those having the general formula:

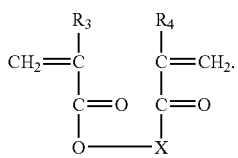

II wherein $R_3$ and $R_4$ are each independently H, a $C_{1-30}$ straight or branched chain alkyl, aryl, or aralkyl; and X is $[(CH_2)_nO_y]_z$, wherein x is 1-20, and y is 1-20, and z is 1-100. Particularly preferred are difunctional acrylates and methacrylates, such as the compound of formula II above wherein $R_3$ and $R_4$ are $CH_3$ and X is $[(CH_2)_xO_y]_z$ wherein x is 14; and y is 1-6; and z is 1-10.

Particularly preferred are difunctional acrylates and methacrylates, such as the compound of formula II above wherein $R_3$ and $R_4$ are $CH_3$ and X is $[(CH_2)_xO_y]_z$ wherein x is 2; and y is 1, and z is 4. The polymerizable compositions preferably contain 0.1-25%, preferably 0.5-20%, more preferably I-15% by weight of a difunctional monomer. Particularly preferred is where the difunctional monomer is an ethylene glycol dimethacrylate. Most preferred is where the difunctional monomer is tetraethylene glycol dimethacrylate.

Trifunctional and polyfunctional monomers are also suitable for use in the polymerizable monomer compositions of the invention. Examples of such monomers include acrylates and methacrylates such as trimethylolpropane trimethacrylate or trimethylolpropane triacrylate. The preferred compositions of the invention contain 0.001-5%, preferably 0.005-4%, more preferably 0.01-3% by weight of a polyfunctional monomer such as trimethylolpropane trimethacrylate ester or trimethylolpropane triacrylate ester.

Polymerization Accelerators

The monomeric compositions of the invention may contain 0.001-5%, preferably 0.001-4%, more preferably 0.005-3% by weight of a polymerization accelerator, or catalyst, which is preferably an aromatic or aliphatic tertiary amine. Suitable aliphatic or aromatic tertiary amines include those set forth on pages 1532-1534 of the *C.T.F.A. Cosmetic Ingredient Dictionary and Handbook*, Seventh Edition, 1997, which is hereby incorporated by reference. Preferred are aromatic tertiary amines such as N,N-di($C_{1-6}$) alkyl-p-toluidines such as N,N-dimethyl-p-toluidine, N,N-diethyl-p-toluidine; or N,N-di ($C_{1-6}$) alkyl anilines such as N,N-dimethyl aniline. The preferred accelerator is N,N-dimethyl-p-toluidine.

The amine polymerization accelerator acts as a catalyst in chain extension and/or cross-linking of the monomers in the monomer composition. In the case where the polymerizable composition is polymerized by chemical means in a liquid/powder system, the most commonly used accelerator is an amine, as mentioned above, in combination with an organic peroxide such as benzoyl peroxide. Generally, the amine accelerator is found in the monomer composition and the peroxide in the powdered composition which is mixed with the monomer composition to cause polymerization immediately prior to application of the composition to the nail, as further discussed herein.

Plasticizer

The compositions of the invention may contain 0.001-5%, preferably 0.001-4%, more preferably 0.005-3% by weight of a plasticizer. The plasticizer causes the polymerized nail structure to have improved flexibility and reduced brittleness. Suitable plasticizers are esters, low volatility solvents, or non-ionic materials such as nonionic organic surfactants or silicones.

Suitable esters include those having the general structure RCO—OR' where RCO— represents the carboxylic acid radical and where —OR' is the alcohol residue. Preferably R and R' are fatty radicals, having 6 to 30 carbon atoms, and may be saturated or unsaturated. Examples of suitable esters are those set forth on pages 1558 to 1564 of the *C.T.F.A. Cosmetic IngredientDictionary and Handbook*, Seventh Edition, 1997, which is hereby incorporated by reference. In the preferred compositions of the invention, the plasticizer is an ester of the formula RCO—OR' wherein R and R' are each independently a straight or branched chain $C_{6-30}$ alkyl. Preferably, R is $C_{6-12}$ alkyl, preferably a $C_8$ alkyl, and R' is a $C_{16-22}$, preferably $C_{18}$ alkyl. The preferred plasticizer is isostearyl isononanoate.

Other suitable plasticizers are low volatility solvents such as paraffinic hydrocarbons, butyrolactone, xylene, methyl isobutyl ketone, and the like. Suitable paraffinic hydrocarbons include isoparaffins having 7 to 14 carbon atoms. Examples of other solvents include those set forth on pages 1670 to 1672 of the *C.T.F.A Cosmetic Ingredient Dictionary and Handbook*, Seventh Edition, 1997, which is hereby incorporated by reference. Particularly preferred is butyrolactone.

Also suitable as plasticizers are various silicones. Suitable silicones include volatile or non-volatile silicone fluids, silicone resins, and silicone semi-solids or solids.

Volatile silicones are linear or cyclic silicones having a measurable vapor pressure, which is defined as a vapor pressure of at least 2 mm. of mercury at 20° C. Examples of volatile silicones are cyclic silicones having the general formula:

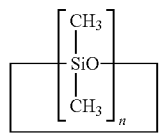

where n=3-7.

Also, linear volatile silicones that may be used in the compositions of the invention have the general formula:

where n=0-7, preferably 0-5.

Suitable water insoluble nonvolatile silicone fluids including polyalkyl siloxanes, polyaryl siloxanes, polyalkylaryl siloxanes, polyether siloxane copolymers, amine-functional silicones, and mixtures thereof. Such silicones have the following general formula:

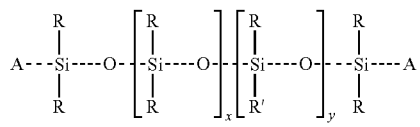

wherein R and R' are each independently alkyl, aryl, or an alkyl substituted with one or more hydroxyl or amino groups, and x and y are each independently 0-100,000, with the proviso that x+y equals at least one and A is siloxy endcap unit. Preferred is where A is methyl, R is methyl, and R' is an $C_{1-4}$ alkyl substituted with at least one hydroxyl groups, most preferably a silicone having the formula:

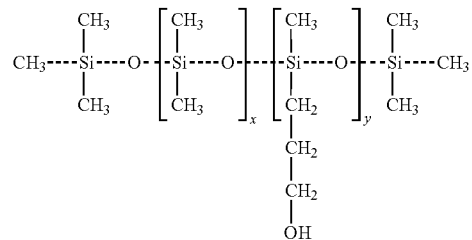

which is known by the CTFA name hydroxypropyldimethicone.

Other compounds known in the art to have a plasticizing effect are also suitable for use as the plasticizer component. Preferred is where the plasticizer component is a mixture of esters, silicones, and solvents.

U.V. Absorbers

The compositions of the invention may contain one or more U.V. absorbers, which assist in reducing the yellowing which is often seen in artificial nails. The U.V. absorber has the ability to convert incident U.V. radiation into less damaging infrared radiation (heat), or visible light. A recommended amount of U.V. absorber is 0.001-5%, preferably 0.005-4%, more preferably 0.01-3% by weight of the total composition. Suitable U.V. absorbers include hydroxy benzotriazole compounds such as 2-(2-hydroxy-5'-methylphenyl)benzotriazole, in addition to the Benzophenones 1-12, 3-benzylidene camphor, benzyl salicylate, borneolone, bumetrizole, PABA, butyl PABA, butyl methoxydibenzoymethane, cinoxate, DEA-methoxycinnamate, Dibenzoxazoyl naphthalene, digalloyl trioleate, diisopropyl methyl cinnamate, and so on. Preferred are the hydroxy benzotriazole compounds, in particular 2-(2-hydroxy-5'-methylphenyl)benzotriazole.

Polymerization Regulators

It may also be desirable to include in the composition one or more compounds which assist in regulating polymerization of the monomer composition. A polymerization regulator assists in preventing the polymerization of the monomer composition from occurring too quickly. Hydroquinone and similar materials are suitable polymerization regulators. Suggested ranges of polymerization regulators are from about 0.0001-5%, preferably 0.001-4%, more preferably 0.005-3% by weight of the total composition.

The preferred polymerizable compositions of the invention comprise:

1-20% of a multicarbonyl-vinyl containing monomer having the formula:

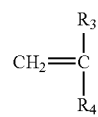

wherein $R_3$ is H, a $C_{1-30}$ straight or branched chain alkyl, aryl, aralkyl; and

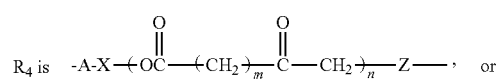

-continued

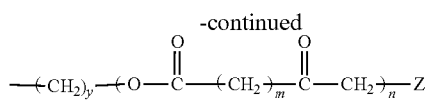

wherein

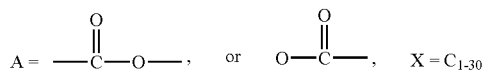

straight or branched chain alkyl, m is 1 to 5, n is 1 to 30, y is 0 to 50; and Z=H or a $C_{1-30}$ straight or branched chain alkyl; 25-95% of a monoethylenically unsaturated monofunctional monomer having the general formula:

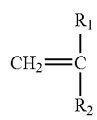

wherein $R_1$ is H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is H, a $C_{1-30}$ straight or branched chain alkyl, pyrrolidone, or a substituted or unsubstituted aromatic, alicylic, or bicyclic ring where the substitutents are $C_{1-30}$ straight or branched chain alkyl which may be substituted with one or more hydroxyl groups, or $[(CH_2)_mO]_nH$ wherein m is 1-20, and n is 1-200.

Polymer Powders

The polymerizable composition of the invention may be polymerized by exposure to radiant energy, such as heat or U.V. light. If so, the composition is applied to nails and shaped in the desired configuration. The coated nails are exposed to radiant energy, and polymerization occurs. On the other hand, the most common method is for the polymerizable composition to be mixed with a powder comprised of polymer powders in what is referred to as the "powder/liquid" method of polymerization. Suitable polymer powders are preferably polymers or copolymers which contain at least some ethylenic unsaturation to permit cross-linking. The polymer powder mixture is generally comprised of a linear particulate chain-extended or cross-linked acrylate or methacrylate polymer, which may be in the random or block copolymer form. Most typically the acrylate or methacrylate polymer is ethyl or methyl methacrylate or ethyl or methyl acrylate, or a combination of one or more of these polymers. Most often a copolymer of ethyl and methyl methacrylate is used. The polymer powder composition may also contain a polymerization accelerator, or catalyst, which is designed to work in conjunction with the accelerator found in the polymerizable composition. Most preferred is a peroxide, such as benzoyl peroxide. The polymer powder may also contain other ingredients such as titanium dioxide and other dyes and/or pigments.

In the preferred embodiment of the invention, polymerizable composition is polymerized using the "powder/liquid" method. Immediately prior to use, an appropriate amount of the polymerizable composition is poured into a dish or other appropriate vessel. A brush or other shaping tool is dipped into the composition to form a small bead on the tip of the tool. This bead is then dipped into the Polymer powder mixture, which is in a separate dish. Upon dipping the bead of liquid monomer on the brush into the Polymer powder material, a doughy, adherent, agglomerated mass of particles is formed at the tip of the shaping tool. Alternatively, the powder can be slurried in the liquid to obtain a doughy mass, and the shaping tool is dipped into the dough. Generally a ratio of 0.2 to 1.3 parts of polymer powder to 1 part of the liquid monomer composition will provide suitable polymerization. The liquid monomer softens and partially dissolves the powder. The tip of the shaping tool, with its load of doughy material is then used to sculpt a new nail shape on the nail surface. The peroxide in the powder and the amine in the liquid monomer act together to catalyze polymerization of the monomer composition to result in an artificial nail structure, which is then shaped and polished as desired. In order for the polymerizable composition to exhibit a desirable workability, the composition should be such that when a Ito 0.5, respectively, mixture of the polymerizable composition and the above mentioned powdered catalyst are mixed and stored at 15° C., the mixture should gel to a viscosity of 100,000 centipoise in 400 to 1400 seconds, preferably 600 to 1200 second, most preferably 800 to 1000 seconds.

The above method describes use of the polymerizable composition when polymerization by chemical means is used. However, as previously noted, the polymerizable composition may be polymerized by other methods, such as by exposure to UV light, heat, and so on, in which case it may not be necessary to use the powdered mixture to initiate polymerization.

The Artificial Nail Structure

The invention is also directed to an artificial nail structure having a thickness of 10-60, preferably 20-50, more preferably 25-45 mils, and a modulus of elasticity of about 550-800 $N/m^2$, comprising a copolymer of at least one ethylenically unsaturated monomer and a multicarbonyl vinyl-containing monomer.

The stiffness is as measured in Newtons per meter as defined by the ASTM test method for the three point bend test as described in ATSM Method D 790-86 as mentioned above.

Preferably the artificial nail structure comprises a copolymer of an ethylenically unsaturated monomer of Formula I, above, and a multicarbonyl-vinyl containing monomer having the general formula set forth above. More preferably the artificial nail structure comprises a copolymer of one or more monofunctional ethylenically unsaturated monomers, one or more difunctional ethylenically unsaturated monomers, and one or more tri- or polyfunctional ethylenically unsaturated monomers and the di-carbonyl vinyl containing monomer. Most preferably, the artificial nail structure comprises a copolymer of ethyl methacrylate, methyl methacrylate, hydroxpropyl methacrylate, acetoacetoxyethyl methacrylate, tetraethylene glycol dimethacrylate, and trimethylolpropane trimethacrylate ester. The artificial nail structure of the invention may also be made in a mold, and attached to the fingernail by adhesive or other similar means.

A Method For Reducing Delamination

The invention also comprises a method for reducing, ameliorating, or eliminating delamination of an artificial nail structure from the natural nail surface, wherein said artificial nail structure is obtained by polymerizing on the natural nail surface a polymerizable monomer composition, comprising adding to said polymerizable monomer composition an effective amount of at least one multicarbonyl-vinyl containing monomer. Preferably, the multicarbonyl-vinyl containing monomer is as mentioned herein, and the polymerizable monomer composition comprises at least one ethylenically unsaturated monomer, preferably of Formula I. The amounts which will reduce delamination range from about 1-15% by weight of the total composition of the polymerizable composition. Delamination is inversely related to adhesion. In other words, the greater the adhesion, the less the tendency for delamination.

A Method for Improving Adhesion

The invention also comprises a method for improving adhesion of an artificial nail structure to the nail surface, wherein the artificial nail structure is to be applied by polymerizing on the nail surface a polymerizable monomer composition, comprising adding to said polymerizable monomer composition an effective amount of at least one multicarbonyl-vinyl containing monomer. The multicarbonyl-vinyl containing monomer and other components of the composition are as set forth herein. The resulting artificial nail structure exhibits improved adhesion to the nail surface when compared to nail compositions which do not contain the multicarbonyl-vinyl containing monomer.

A Method for Reducing Premature Gelation

The invention also comprises a method for reducing premature gelation of a liquid monomer composition containing at least one ethylenically unsaturated monomer, comprising adding to said monomer composition an effective amount of at least one multicarbonyl-vinyl containing monomer.

The preferred ethylenically unsaturated monomers and multicarbonyl-vinyl containing monomers are as mentioned herein. The addition of the multicarbonyl-vinyl containing monomer considerably improves gelation time. Generally, polymerizable compositions containing an effective amount of the multicarbonyl-vinyl containing monomer will remain ungelled from 1 to 20, preferably 1-10 days longer than similar compositions which do not contain the multicarbonyl-vinyl containing monomer, when maintained at 45° C.

The invention will be further described in connection with the following examples, which are set forth for the purposes of illustration only.

EXAMPLE 1

An artificial nail composition was made as follows:

| | w/w % | |
|---|---|---|
| Ethyl methacrylate | 74.0 | (monomer) |
| Hydroxypropyl methacrylate | 9.798 | (monomer) |
| Acetoacetoxy ethylmethacrylate | 5.0 | (AAEMA monomer) |
| Tetraethylene glycol dimethacrylate | 9.0 | (cross-linkable monomer) |
| N,N-dimethyl-p-toluidine | 1.0 | (accelerator) |
| 2-(2'-hydroxy-5'-methylphenyl) benzotriazole | 0.5 | (U.V. absorber) |
| Isostearyl Isononanoate | 0.2 | (plasticizer) |
| Hydroxypropyl dimethicone | 0.2 | (plasticizer) |
| Butyrolactone | 0.2 | (plasticizer) |
| Trimethylolpropane trimethacrylate ester | 0.1 | (cross-linkable monomer) |
| D&C violet #2 | 0.001 | (colorant) |
| Hydroquinone | 0.001 | (polymerization regulator) |

The above mentioned composition was made by combining the ingredients in the order listed and mixing well. The composition had the consistency of a thick, viscous, liquid. The composition was stored in a brown glass jar.

EXAMPLE 2

Polymerizable compositions in accordance with the invention were tested for pre-mature gelation. Compositions were prepared as follows:

| | w/w % | | | |
|---|---|---|---|---|
| | 1 | 2 | 3 | 4 |
| Ethyl methacrylate | 79. | 72. | 74. | 78.75 |
| Hydroxypropyl methacrylate | 9.798 | 9.798 | 9.798 | 9.798 |
| Tetraethylene glycol dimethacrylate | 9.0 | 9.0 | 9.0 | 9.0 |
| Acetoacetoxyethyl methacrylate | — | 7.0 | 5.0 | 0.25 |
| N,N-dimethyl-p-toluidine | 1.0 | 1.0 | 1.0 | 1.0 |
| 2-(2'-hydroxy-5'-methylphenyl) benzotriazole | 0.50 | 0.50 | 0.50 | 0.50 |
| Trimethylolpropane trimethacrylate ester | 0.10 | 0.10 | 0.10 | 0.10 |
| Butyrolactone | 0.20 | 0.20 | 0.20 | 0.20 |
| Isostearyl isononanoate | 0.20 | 0.20 | 0.20 | 0.20 |
| Hydroxypropyl dimethicone | 0.20 | 0.20 | 0.20 | 0.20 |
| D&C Violet #2 | 0.001 | 0.001 | 0.001 | 0.001 |
| Hydroquinone | 0.001 | 0.001 | 0.001 | 0.001 |

| | w/w % | |
|---|---|---|
| | 5 | 6 |
| Ethyl methacrylate | 78.5 | 78. |
| Hydroxypropyl methacrylate | 9.798 | 9.798 |
| Tetraethylene glycol dimethacrylate | 9.0 | 9.0 |
| Acetoacetoxyethyl methacrylate | 0.50 | 1.0 |
| N,N-dimethyl-p-toluidine | 1.0 | 1.0 |
| 2-(2'-hydroxy-5'-methylphenyl) benzotriazole | 0.50 | 0.50 |
| Trimethylolpropane trimethacrylate ester | 0.10 | 0.10 |
| Butyrolactone | 0.20 | 0.20 |
| Isostearyl isononanoate | 0.20 | 0.20 |
| Hydroxypropyl dimethicone | 0.20 | 0.20 |
| D&C Violet #2 | 0.001 | 0.001 |
| Hydroquinone | 0.001 | 0.001 |

Compositions 1-6 were tested for stability by pouring each sample in 20 mL. borosilicate glass scintillation vials and placing in a 45C.° oven. The samples were checked daily, and the number of days before the composition completely gelled in the container was recorded. This test is a reliable indicator of the tendency of monomer compositions to exhibit premature gelation. The results are as follows:

| Sample # | Vial | No. Days |
|---|---|---|
| 1 | (a) | 5 |
| | (b) | 5 |
| | (c) | 5 |
| | (d) | 6 |
| | (e) | 6 |
| | (f) | 6 |
| | (g) | 7 |
| | (h) | 8 |
| | (i) | 8 |
| | (j) | 8 |
| 2 | (a) | 10 |
| | (b) | 11 |
| | (c) | 11 |
| | (d) | 12 |
| | (e) | 13.5 |
| | (f) | 9 |
| | (g) | 9 |
| | (h) | 12 |

-continued

| Sample # | Vial | No. Days |
|---|---|---|
| | (i) | 12 |
| | (j) | 12.5 |
| 3 | (a) | 19 |
| | (b) | 19 |
| | (c) | 19 |
| | (d) | 19 |
| | (e) | 19 |
| | (f) | 15 |
| | (g) | 18 |
| | (h) | 18 |
| | (I) | 18 |
| | (j) | 18 |
| 4 | (a) | 6 |
| | (b) | 7 |
| | (c) | 8 |
| | (d) | 9 |
| 5 | (a) | 6 |
| | (b) | 7.5 |
| | (c) | 8 |
| | (d) | 10-11 |
| 6 | (a) | 8.5 |
| | (b) | 9 |
| | (c) | 12 |
| | (d) | 12 |

Sample 1, which did not contain the multicarbonyl-vinyl containing monomer gelled in about 5 to 8 days at 45° C. Samples 2-6, which contained varying amounts of the multicarbonyl-vinyl containing monomer, in particular acetoacetoxyethyl methacrylate, gelled in 6 to 19 days at 45° C. Samples 2 and 3, containing 7% and 5% acetoacetoxyethyl methacrylate respectively, exhibited gel times ranging from 9 to 19 days.

EXAMPLE 3

Adhesion of various artificial nails to the nail surface was measured by coating a keratinous substrate with a 25 mil. coating of the composition. A Romulus III Hesiometer was used to cut through the coating on the keratinous substrate, and the force required to cause the coating to become disengaged from the substrate was recorded in joules per square meter (joules/m$^2$). The results are as follows:

| Product | No Primer | Primer* |
|---|---|---|
| EXAMPLE 2 (1) | 387.9 | 534 |
| EXAMPLE 2 (2) | 811 | 590 |
| EXAMPLE 2 (3) | 593 | 542 |
| Tammy Taylor | 239 | 285 |
| OPI L-3000 | | 336 |
| Kismet | 149.4 | 203 |
| Premium | | 276 |
| Polymax/OPI | 144.7 | 195 |
| Choice | | 330 |
| Cosmic | | 514 |
| Galaxy | | 436 |
| Simplicite | | 250 |
| European Touch | | 320 |

*The primer composition containing 100% by weight methacrylic acid was applied to nails prior to applying the liquid monomer composition.

The results show that the polymerizable compositions of the invention show improved adhesion to keratin either with or without a prior application of primer composition to the nail.

EXAMPLE 4

Compositions were prepared as follows:

| | w/w % | | | |
|---|---|---|---|---|
| | #1 | #2 | #3 | #4 |
| Acetoacetoxyethylmethacrylate | 98 | 96 | 97.5 | 96 |
| Dimethyl-p-toluidine | 1 | 2 | 1.5 | 1 |
| Tetraethylene glycol dimethacrylate | 0 | 0 | 0 | 3 |
| UV-9* | 1 | 2 | 1 | 0 |
| Violet dye | 0.0002 | 0.0004 | 0 | 0 |

*Ultraviolet 9, a U.V. Absorber.

The above ingredients were mixed together. One part of the composition was combined with one part of a 100% poly (ethylmethacrylate) homopolymer and mixed. The compositions were applied to nails and shaped to form artificial nail structures.

EXAMPLE 5

Compositions (2) and (3) of Example 2 were tested on panelists. Trained nail technicians applied Composition (2) to 14 panelists, and Composition (3) to 13 panelists. The technicians applied the material in the usual manner, using the liquid/powder method of polymerization. The technicians were then asked to answer a series of questions as follows:

1. How is the overall retention of the artificial nail? (retention, or adhesion, is how well the artificial nail adheres to the nail surface)

| % Panelists who said: | (2) | (3) |
|---|---|---|
| Very High | 64.3 | 53.8 |
| High | 14.3 | 30.8 |
| Medium | 7.1 | 0 |
| Low | 7.1 | 0 |
| Very Low | 0 | 0 |
| No Answer | 7.1 | 15.4 |

2. Do any of your clients have separation at the free edge? (Refers to separation of the artificial nail from the natural nail surface at the nail tip, also referred to as delamination)

| % Panelists who said: | (2) | (3) |
|---|---|---|
| Yes | 7.1 | 0 |
| No | 71.4 | 84.6 |
| No Answer | 21.4 | 15.4 |

3. Did any of your clients have lifting? If so where? (Refers to lifting of the artificial nail from the nail surface)

| % Panelists who said: | (2) | (3) |
|---|---|---|
| None yet | 35.7 | 84.6 |
| Other | 50.0 | 15.4 |
| No Answer | 14.3 | 0 |

4. Did any of your clients experience breakage? (refers to breaking of the artificial nail)

| % Panelists who said: | (2) | (3) |
|---|---|---|
| No | 57.1 | 69.2 |
| Other | 35.7 | 30.8 |

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for reducing or eliminating delamination of an artificial nail structure from a natural nail surface, wherein said artificial nail structure is obtained by polymerizing on the natural nail surface a polymerizable monomer composition, said method comprising adding to said polymerizable monomer composition an effective amount of at least one multicarbonyl-vinyl containing monomer and at least one other ethylenically unsaturated monomer.

2. A method for improving adhesion of an artificial nail structure to the nail surface, wherein the artificial nail structure has been applied by polymerizing on the nail surface a polymerizable monomer composition, comprising adding to said polymerizable monomer composition an effective amount of at least one multicarbonyl-vinyl containing monomer and at least one other ethylenically unsaturated monomer.

3. A method for applying an artificial nail to a nail surface comprising applying to said nail surface a polymerizable composition containing at least one monoethylenically unsaturated vinyl monomer that contains two or more carbonyl groups and at least one other ethylenically unsaturated monomer.

* * * * *